(12) United States Patent
Winfield et al.

(10) Patent No.: US 12,172,033 B2
(45) Date of Patent: Dec. 24, 2024

(54) PATIENT POSITIONING FOR RADIOTHERAPY TREATMENT

(71) Applicant: Elekta Limited, Crawley (GB)

(72) Inventors: Colin Winfield, Crawley (GB); Rui Liu, Beijing (CN)

(73) Assignee: Elekta Limited, Crawley (GB)

( * ) Notice: Subject to any disclaimer, the term of this patent is extended or adjusted under 35 U.S.C. 154(b) by 222 days.

(21) Appl. No.: 17/997,613

(22) PCT Filed: Apr. 29, 2021

(86) PCT No.: PCT/EP2021/061351
§ 371 (c)(1),
(2) Date: Oct. 31, 2022

(87) PCT Pub. No.: WO2021/219830
PCT Pub. Date: Nov. 4, 2021

(65) Prior Publication Data
US 2023/0211182 A1    Jul. 6, 2023

(30) Foreign Application Priority Data
Apr. 29, 2020 (GB) .................................. 2006317

(51) Int. Cl.
*A61N 5/10* (2006.01)
(52) U.S. Cl.
CPC ......... *A61N 5/1049* (2013.01); *A61N 5/1037* (2013.01); *A61N 5/107* (2013.01)
(58) Field of Classification Search
CPC .... A61N 5/1049; A61N 5/1037; A61N 5/107; A61N 2005/105; A61N 2005/1054;
(Continued)

(56) References Cited

U.S. PATENT DOCUMENTS 6,094,760 A     8/2000  Nonaka et al.
10,137,315 B2 * 11/2018  Vilsmeier .............. A61N 5/103
(Continued)

FOREIGN PATENT DOCUMENTS

EP     2289597 A1    3/2011
EP     3300770 A1    4/2018
(Continued)

OTHER PUBLICATIONS

"International Application Serial No. PCT/EP2021/061351, International Search Report dated Apr. 8, 2021", (Apr. 8, 2021), 6 pgs.
(Continued)

*Primary Examiner* — Kiho Kim
(74) *Attorney, Agent, or Firm* — Schwegman Lundberg & Woessner, P.A.

(57) ABSTRACT

Disclosed herein is a method of positioning a patient for radiotherapy treatment using a radiotherapy system. The method comprises determining a first target position for the patient for radiotherapy treatment; implementing a spatial relationship between the patient and at least a part of the radiotherapy device, at a first time ($t_1$), according to the first target position; providing radiotherapy treatment to the patient; determining a current position of the patient, at a second, subsequent time ($t_2$); and determining whether a change of a spatial relationship between the patient and at least a part of the radiotherapy device should be made, according to the first target position.

20 Claims, 7 Drawing Sheets

(58) Field of Classification Search
CPC .......... A61N 5/1067; A61N 2005/1057; A61N 2005/1061; A61N 5/103; A61N 5/1048; A61N 5/1069; A61N 2005/0642
See application file for complete search history.

(56) References Cited

U.S. PATENT DOCUMENTS

| | | |
|---|---|---|
| 2018/0133508 A1 | 5/2018 | Pearce et al. |
| 2019/0069870 A1 | 3/2019 | Igler |

FOREIGN PATENT DOCUMENTS

| | | | | |
|---|---|---|---|---|
| EP | 3550327 A1 | 10/2019 | | |
| GB | 2530254 A | * 3/2016 | ............... | A61N 5/10 |
| WO | WO-2006113323 A2 | 10/2006 | | |
| WO | WO-2017202725 A1 | 11/2017 | | |

OTHER PUBLICATIONS

"International Application Serial No. PCT/EP2021/061351, International Search Report dated Apr. 8, 2021", (Apr. 8, 2021), 10 pgs.
"United Kingdom Application Serial No. 2006317.8, Examination Report dated Oct. 29, 2020", (Oct. 29, 2020), 8 pgs.

* cited by examiner

PATIENT POSITIONING FOR RADIOTHERAPY TREATMENT

PRIORITY APPLICATIONS

This application is a U.S. National Stage Filing under 35 U.S.C. § 371 from International Application No. PCT/EP2021/061351, filed on Apr. 29, 2021, and published as WO2021/219830 on Nov. 4, 2021, which claims the benefit of priority to United Kingdom Application No. 2006317.8, filed on Apr. 29, 2020; the benefit of priority of each of which is hereby claimed herein, and which applications and publication are hereby incorporated herein by reference in their entireties.

FIELD

This disclosure relates to methods of positioning a patient for radiotherapy treatment using a radiotherapy device. This disclosure further relates to determination of a patient position for improved radiotherapy treatment.

BACKGROUND

Radiotherapy can be described as the use of ionising radiation, such as X-rays, to treat a human or animal body. Radiotherapy is commonly used to treat tumours within the body or skin of a patient or subject. In such treatments, ionising radiation is used to irradiate, and thus destroy or damage, cells which form part of the tumour.

A radiotherapy device typically comprises a gantry which supports a treatment apparatus that comprises a beam generation system, or other source of radiation, which is rotatable around a patient. For example, for a linear accelerator (linac) device, the beam generation system may comprise a source of radio frequency energy, a source of electrons, an accelerating waveguide, and beam shaping apparatus.

For the purposes of radiotherapy treatment, it is desirable to deliver a particular dose to a target region, as prescribed by a treatment plan, while minimising the dose to surrounding areas of healthy tissue. Radiotherapy systems typically deliver beams of MegaVolt (MV) radiation energy from different angles to the area to be treated, i.e. the target region. In this way, each portion of healthy tissue surrounding the target region is only exposed to the radiation beam intermittently, at particular angles, whilst the target region is exposed to the MV radiation beam throughout treatment, at every angle.

A patient positioning apparatus (which may comprise a patient positioning surface or patient support surface) may be used to position a patient in a scanning or treatment volume of a radiotherapy device. For example, a patient positioning apparatus may be used to ensure the patient is correctly positioned with respect to a source of therapeutic radiation, in accordance with a patient-specific treatment plan. The patient positioning apparatus may be configured to move the patient in multiple of degrees of freedom. For example, a patient positioning apparatus may be configured to move both vertically and horizontally (i.e. up, down, left, right, forwards and backwards). It may also be configured to tilt and/or rotate about one or more axes. There may also be some space for a patient to physically move him or herself, either deliberately or unconsciously, whilst located on a patient positioning apparatus.

Whilst it is advantageous to be able to move patients in many different ways for radiotherapy treatment; such a wide scope for movement creates an increased need to monitor patient position. It may be appropriate to monitor relatively large-scale movements—for example, to determine whether a patient positioning apparatus has moved a patient in a manner, or to a position, that it is in accordance with instructions provided to it. It may also be appropriate to monitor smaller-scale movements, that arise from 'real-world' conditions. For example, it may be appropriate to monitor for the effects of apparatus sag or flex, and/or for patient movements.

The present inventors have addressed these matters.

SUMMARY

In general terms; methods, apparatus and systems are provided herein that enable accurate monitoring, and feedback, regarding the position of a patient, and/or of a patient support surface, immediately before and/or during radiotherapy treatment. The monitoring and feedback may be provided during pre-treatment imaging, or set-up, and may continue throughout the delivery of the radiotherapy treatment. The monitoring and/or feedback may be continuous or non-continuous.

The methods, apparatus and systems described herein can enable accurate positioning of a patient at the beginning of radiotherapy treatment, in accordance with a treatment plan, which may be patient-specific, and accurate and efficient movement of the patient to a different position, if required in accordance with the treatment plan, during radiotherapy treatment. The methods, apparatus and systems described herein can also account for real world effects such as 'sag', 'stress', 'strain' or 'flex' of parts of the radiotherapy device, such as the patient support surface (or patient positioning surface). They may also account for patient movement, before and/or during radiotherapy treatment.

The methods, apparatus and systems described herein may also enable checking and, if appropriate, correction of the position or location of a patient support surface (or patient positioning surface), during a radiotherapy treatment. They may enable monitoring and, if appropriate, correction of patient position during static radiotherapy treatment, in which a patient is still whilst treatment is being applied, and in dynamic radiotherapy treatment, during which the patient support surface is being continuously moved.

The methods, apparatus and systems described herein may provide a self-checking system, which can automatically or semi-automatically check patient (and/or patient support surface) position, and make appropriate corrections, during radiotherapy treatment. Thus, a self-contained (holistic) patient movement and monitoring system may be provided, which enables the accurate provision of both treatment plan-specific movement and movement that accounts for real-world movements or changes, before and during radiotherapy treatment.

The system may comprise sensors mounted below the patient support surface, such as but not limited to floor-mounted sensors, which do not suffer from significant 'line of sight' restrictions.

According to an aspect, a method is provided of positioning a patient for radiotherapy treatment using a radiotherapy system. The method comprises determining a first target position for the patient for radiotherapy treatment and implementing a spatial relationship between the patient and at least a part of the radiotherapy device, at a first time ($t_1$), according to the first target position, and providing radiotherapy treatment to the patient. The method further comprises determining a current position of the patient, at a second, subsequent time ($t_2$) and determining whether a change of a spatial relationship between the patient and at least a part of the radiotherapy device should be made, according to the first target position.

The steps of determining a current position of the patient and determining whether a further change of a spatial relationship between the patient and at least a part of the radiotherapy device should be made, according to the first target position, may be repeated at a third time ($t_3$), subsequent the second time ($t_2$). These steps may be repeated multiple times, during radiotherapy treatment.

The method may comprise implementing a change to a spatial relationship between the patient and at least a part of the radiotherapy device, in accordance with the determination made. For example, the change may involve moving a support surface, on which the patient is located. For example, the change may involve moving another part of the radiotherapy system.

The method may further comprise, once a current position of the patient is determined, at the second, subsequent time ($t_2$), conducting a comparison of the current position of the patient, at the second time ($t_2$), and the first target position for the patient. The comparison may determine whether there is a difference between the current position and the first target position and what the size and nature of that difference is.

The radiotherapy system may comprise a controller. The method may further comprise determining whether a change should be made to a computation or a process that the controller is arranged to carry out, based on a comparison of the current position of the patient, at the second time ($t_2$), and the first target position for the patient. For example, a mathematical formula that the controller uses may have to be changed. For example, a tolerance level or margin of error, which the controller applies to computations, may have to be altered. For example, the controller may update a map or an information store to correct a previously-assumed or previously-obtained position of the patient with an updated position of the patient, as determined at time $t_2$.

The method may include determining a second, different target position for the patient. The method may further include implementing a spatial relationship between the patient and at least a part of the radiotherapy device, at a given time ($t_x$), according to the second target position, and providing radiotherapy treatment to the patient. The method may further comprise determining a current position of the patient, at another, subsequent time ($t_y$), and determining whether a change of a spatial relationship between the patient and at least a part of the radiotherapy device should be made, according to the second target position.

The first target position for the patient may be comprised within a patient-specific treatment plan. A second target position (or any other subsequent target position) for the patient may be comprised within a patient-specific treatment plan. Alternatively, a second or subsequent target position may be determined to account for or compensate for any difference that has been determined between an actual position of the patient, at a particular time, and a previously-set target patient position for that time.

The patient may be supported by a patient support surface (or patient positioning surface) for radiotherapy treatment and one or more sensors may be provided, located below the patient support surface. There may be one or more markers provided, on an underneath surface of the patient support surface, wherein the sensors are arranged to detect the presence of said one or more markers.

The step of determining a current patient position may comprise receiving a signal from the one or more sensors located below the patient support surface and using the received signal(s) to determine a position of at least part of the patient.

The steps of determining a current position of the patient and determining whether a change of a spatial relationship between the patient and at least a part of the radiotherapy device should be made, according to a target position, may be repeated multiple times, during radiotherapy treatment. An amendment may be made, to the target position, during radiotherapy treatment, and any subsequent determinations may be made according to the amended target position.

According to an aspect, a data processing apparatus for a radiotherapy system is provided, the data processing apparatus comprising a processor configured to perform the method of any of the above aspects.

According to an aspect, a radiotherapy system is provided, comprising a radiotherapy device and a controller; the radiotherapy device comprising: a radiotherapy beam generation apparatus; a moveable patient support surface; an actuator for moving the moveable patient support surface; and one or more sensors provided below an underneath surface of the moveable patient support surface. The controller is configured to carry out the method of any of the above-described aspects.

The controller may be further configured to control actuation of the actuator in order to move the moveable patient support surface, according to the first target position for the patient for radiotherapy treatment.

The method according to one or more of the above-described aspects may be executed by a computer.

According to an aspect, a computer readable storage medium is provided, comprising computer-executable instructions which, when executed by a computer, cause the computer to carry out the method of any of the above-described aspects.

According to an aspect, a data carrier signal may be provided, carrying computer-executable instructions which, when executed by a computer, cause the computer to carry out the method of any of the above-described aspects.

Although certain aspects above and examples or embodiments below may be described in isolation, it should be understood that any combination of aspects, arrangements, examples and embodiments is contemplated, except when explicitly described as being mutually exclusive to one another.

FIGURES

Specific embodiments are now described, by way of example only, with reference to the drawings, in which.

DETAILED DESCRIPTION

Figure 1:
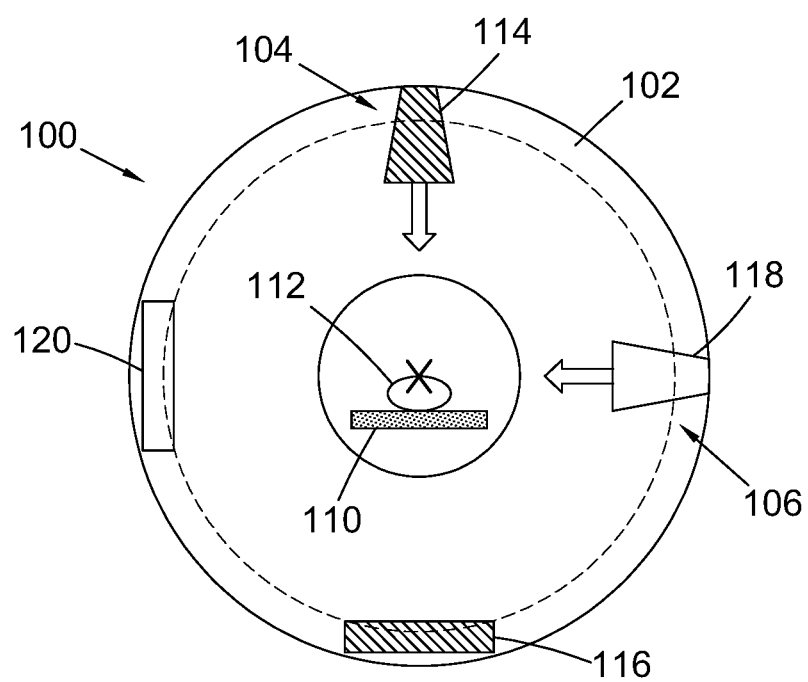
FIG. 1 shows a cross sectional view of a radiotherapy device.

FIG. 1 shows an Image Guided Radiotherapy (IGRT) device 100, in cross section. This is shown by way of example only. The methods described herein may also be applied to other types of radiotherapy device.

The IGRT device 100 in FIG. 1 comprises a rotatable gantry 102, to which are affixed a treatment apparatus 104 and an imaging apparatus 106. In this example, the treatment apparatus 104 and the imaging apparatus 106 are rotatable with the gantry 102, i.e. they rotate as the gantry 102 rotates. Positioned generally along an axis 'X' central to the gantry is a patient support surface 110 upon which a patient 112 lies, for radiotherapy treatment. The patient support surface 110 may be referred to as a 'patient support surface' or as a 'patient positioning surface' or as a 'table' or as a 'couch'.

The patient support surface 110 is shown in FIG. 1 as being located within an opening that is defined, in this example, substantially central to the gantry 102. This should be regarded as illustrative only, and as a non-limiting example of one type of radiotherapy device. As the skilled reader will be aware; there are other types of radiotherapy device, which do not have a central opening such as the one shown in FIG. 1. In some cases, such as a conventional Linear Accelerator (LINAC) radiotherapy device, a patient may mount the patient support surface when it is already located at a treatment position, substantially at the isocentre of the treatment beam. The methods described herein may be applied to any type of radiotherapy device.

The treatment apparatus 104 is configured to direct a treatment beam of therapeutic radiation towards a treatment volume of the radiotherapy device 100. The treatment apparatus 104 comprises a treatment beam source 114 and a treatment beam target 116. The treatment beam source 114 is configured to emit or direct therapeutic radiation, for example MV energy radiation, towards the patient 112. As the skilled person will know, the treatment beam source 114 may comprise an electron source, a linac (linear accelerator) for accelerating electrons toward a heavy metal, e.g. tungsten, target to produce high energy photons, and a collimator configured to collimate the resulting photons and thus produce a treatment beam. For reasons of clarity and brevity, these components are collectively referred to herein as the treatment beam source 114. Once the treatment radiation has passed from the treatment beam source 114 and through the patient 112, the radiation continues towards treatment beam target 116, where it is blocked or absorbed. The treatment beam target 116 may include an imaging panel (not shown). The treatment beam target 116 may therefore form part of an electronic portal imaging device (EPID). EPID's are generally known to the skilled person and will not be discussed in detail herein.

The imaging apparatus 106 comprises an imaging beam source 118 and an imaging panel 120. The imaging beam source 118 is configured to emit or direct imaging radiation, for example X-rays and/or kV energy radiation, towards the patient 112. As the skilled person will know, the imaging beam source 118 may be an X-ray tube or another suitable source of X-rays. The imaging beam source 119 is configured to produce kV energy radiation. Once the imaging radiation has passed from the imaging beam source 118 and through the patient 112, the radiation continues towards the imaging panel 120. The imaging panel 120 may be referred to as a radiation detector, or a radiation intensity detector.

The imaging panel 120 is configured to produce signals indicative of the intensity of radiation incident on the imaging panel 120. In use, these signals are indicative of the intensity of radiation which has passed through the patient 112. These signals may be processed to form an image of the patient 112. This process may be described as the imaging apparatus 106 and/or the imaging panel 120 capturing an image. The methods described herein do not rely on the presence of an imaging apparatus as just described. However, as the skilled reader will know, many radiotherapy devices comprise such an imaging apparatus.

In FIG. 1, the treatment apparatus 104 and the imaging apparatus 106 are mounted on the gantry 102 such that a treatment beam travels in a direction that is generally perpendicular (i.e. at right angles) to that of the imaging beam. However other relative positions of treatment apparatus and imaging apparatus are contemplated.

The patient support surface 110 in FIG. 1 is configured to be moveable from being substantially outside the opening, to being substantially inside the opening. When it is substantially outside the opening, a patient (or 'subject') can mount the patient support surface 110. The patient support surface 110, with the patient, can then be moved inside the opening, in order for the patient to be imaged and/or treated using the radiotherapy imaging and/or treatment apparatus. Again, it should be noted that FIG. 1 is a non-limiting example of one possible type of radiotherapy device, to which the present disclosure relates. Other types of radiotherapy device are also contemplated, including those which do not have an opening as shown in FIG. 1, and those which do not have to be moved, between a patient-mounting position and a patient-treatment position. That is; in some cases, the patient may mount the patient support surface when it is already in position, for patient radiotherapy treatment to commence.

In general terms; a patient support surface (or patient positioning surface) such as the patient support surface 110 of FIG. 1 may be moveable in a variety of directions and/or manners. These will be known to the skilled reader. They are summarised briefly below in relation to the patient support surface 110 FIG. 1, but are also applicable to other types of patient support surface and to other types of radiotherapy device and to other radiotherapy configurations.

For example, the patient support surface 110 may be moveable in a substantially vertical plane, wherein it may, for example, be controlled to be quite low to enable a patient to more easily mount and/or dismount the patient support surface 110, and it may be raised to a higher position, with the patient mounted thereon, for radiotherapy treatment.

For example, the patient support surface 110 may be moveable substantially from left to right, or 'laterally', in a substantially horizontal plane. For example, the patient support surface 110 may be moveable substantially forwards and backwards, in a substantially horizontal plane. It may be movable in a forwards-to-backwards manner, on a relatively large scale, for example, for moving into and out of an opening. A patient support surface may also be moveable in a forwards-to-backwards manner by relatively small (e.g. by incremental) amounts, to assist with more accurate patient positioning for radiotherapy treatment. In some embodiments, oblique movements (i.e. movements at an angle to both the forwards-to-backwards and left-to-right axes in a substantially horizontal plane) of the patient support surface 110 may be possible.

The patient support surface 110 may be substantially flat, or planar. It may be single piece or it may comprise multiple sections, which may be connected together. The patient support surface may comprise one or more hinges or dividers, to separate it into discrete sections, along its length (i.e. along its major axis, which in FIG. 1 extends perpendicular to the cross sectional plane). One or more of those discrete sections may be moveable with respect to one or more of the respective other sections. For example, it may be possible to pivot (or 'tilt' or 'rotate') one section to be at a non-parallel angle, relative to one or more of the respective others. For example, a section of the patient support surface 110 that supports the patient's head may be tiltable upwards, for enhanced patient comfort. Alternatively, an accessory may be placed onto the main patient support surface 110, so that the patient support surface 110 itself does not move in sections but the accessory is mounted and performs those adjustments. For example, a section or accessory that supports a part of the patient that comprises a tumour or other target region may be tilted, relative to one or more of the respective others (or relative to the main body of the patient support surface 110), in order to better position the target area, relative to the treatment beam or to move some parts of the patient's anatomy (such as their arms) out of the path of a treatment beam.

Figure 2:
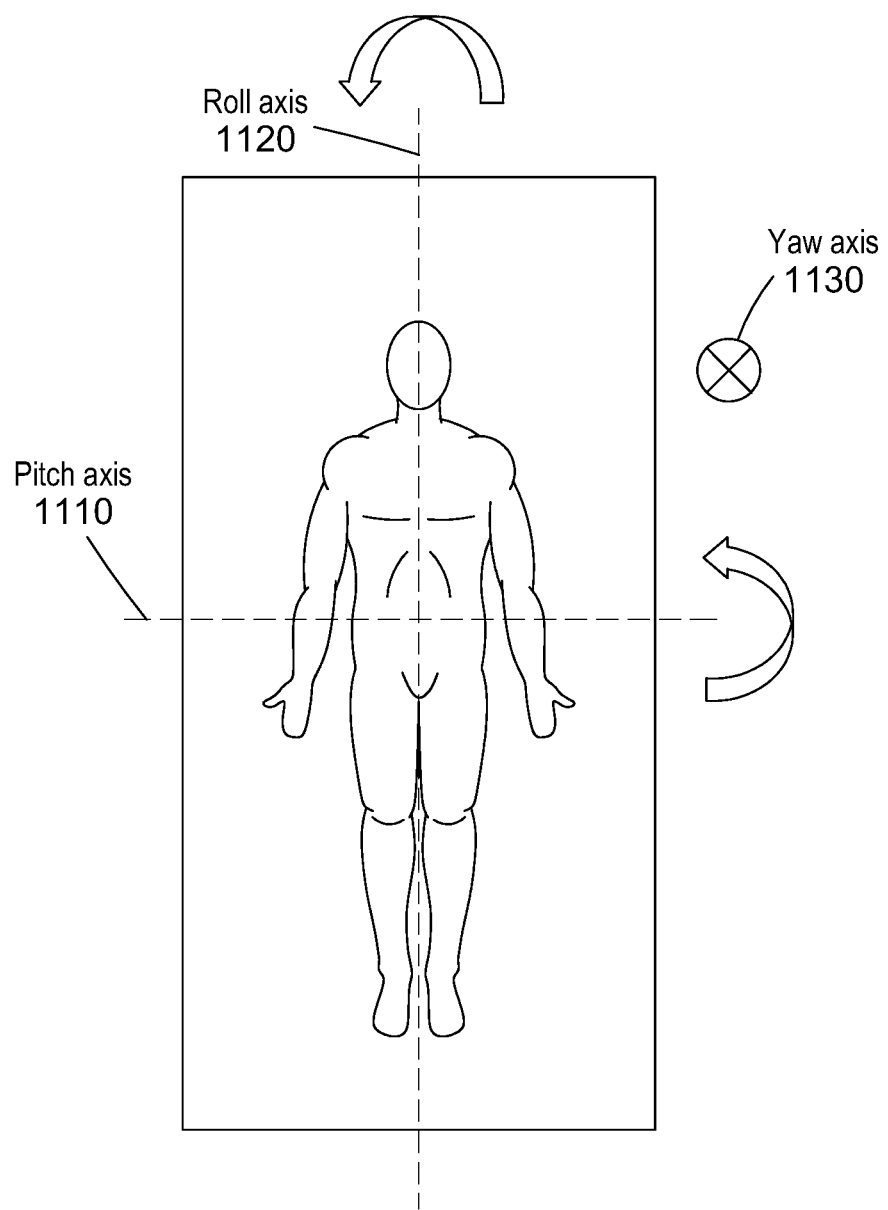
FIG. 2 shows a plan view of a patient on a patient support surface.

The patient support surface 110 may also be rotatable about one or more of its axes. Three possible rotational axes are depicted in FIG. 2, by way of example, relative to a patient support surface such as the patient support surface 110 of FIG. 1. The axes may be referred to as 'x', 'y', and 'z' axes or as 'roll', 'pitch' and 'yaw' axes, respectively. In the example of FIG. 2: the roll axis 1120 extends substantially front to back, i.e. along the line between the patient's head and his or her toes. It may also be referred to as a 'major' axis, in a substantially horizontal plane. The pitch axis 1110 extends substantially left to right, from one side of the patient to the other. It may also be referred to as a 'minor' axis, in a substantially horizontal plane. The yaw axis 1130 extends substantially up and down, from above the patient to below him or her. It will be appreciated that FIG. 2 is illustrative only and any terms such as 'left', 'right', 'side', 'up', 'down', 'front', back', 'vertical', 'horizontal', 'above', and 'below' are used in an illustrative sense only and are not to be regarded as limiting.

Rotation of the patient support surface 110 about one or more axis may be effected in order to better position the patient for radiotherapy treatment. Rotation of the patient support surface 110 about one or more axis may also or instead be effected in order to improve patient comfort and/or because of a patient's clinical requirements.

The movements of the patient support surface 110 can be effected by a suitable actuator, or actuation mechanism, or by any suitable combination of actuators and/or actuation mechanisms, under suitable control of one or more controllers. It will be appreciated that different respective types of movement may be actuated and/or controlled separately to one another. Moreover, movement of different respective parts or sections of the patient support surface 110 may be actuated and/or controlled separately to one another.

One or more controllers may be provided, for controlling the movements of the patient support surface 110. The/each controller may be a computer, processor, or other processing apparatus. The/each controller may be formed by several discrete processors. The/each controller may be communicatively coupled to a memory. The/each controller may be part of a network.

The present inventors have recognised that, whilst it can be highly useful to be able to move a patient, and a patient support surface, in one or more different ways, for radiotherapy treatment; the full benefits of that scope of movement may only be realised if accompanied by accurate and reliable patient position monitoring. That is; one should be able to control actuators to move a patient to a particular position and also to check or verify that he or she is indeed in that position. If a patient is positioned accurately, a radiotherapy treatment beam can be targeted more precisely at one or more target regions within the patient's anatomy. This results in more robust irradiation of the target region(s) and improved shielding of healthy tissues, protecting them from unnecessary irradiation.

The present inventors have recognised that it may not be sufficient to merely check that a patient is in a particular position or location for pre-treatment imaging, or immediately before radiotherapy treatment commences, or immediately after an actuation or movement has occurred. Instead; improvements in accuracy of radiotherapy treatment may be provided by also monitoring patient position, on an ongoing or repeated basis, during radiotherapy treatment. This can enable the detection of patient movement—which may be either deliberate or accidental—and of changes to the apparatus, caused by real-world effects such as sag, flex, stress, strain, creep and so on. Once a movement or a change in position or location (or a difference between an expected position/location and a sensed position/location) is detected, the relevant information can be provided to a controller and a decision may be made (either automatically by a controller and/or with the aid of user input) to ascertain whether a corrective movement should be made, to return the patient and/or the patient support surface to a more appropriate location or position. A feedback loop may be enabled, for ongoing (or repeated) patient position detection, assessment and correction, before and during radiotherapy treatment. This will be discussed in more detail, later in this application.

Alternatively or additionally, when a movement or change in position or location (or a difference between an expected position/location and a sensed position/location) is detected, a controller may make a change to a calculation or plan, or it may make a change to another aspect of the radiotherapy apparatus, other than the patient support surface. For example, a change/difference in patient position may prompt a controller to adjust the treatment apparatus in order to change the location of its beam isocentre, or to amend a treatment plan to account for a change in relative spatial position between a target region within the patient's anatomy and the treatment beam, or to change the position or configuration of the gantry, relative to the patient.

The present inventors have recognised that improvements in the accuracy of patient position monitoring may depend, at least in part, on the nature and/or on the location of the sensors or detectors that are used to detect or monitor patient position. Many currently-known systems suffer from deficiencies. For example, many currently-known systems use stereoscopic cameras, mounted to the ceiling in a radiotherapy environment. Such stereoscopic cameras typically are expensive and require frequent calibration and quality assurance (QA), to ensure that the position of the patient support surface is accurately 'known' to them. Such calibration and QA procedures usually have to happen 'offline', when a patient is not present and the radiotherapy apparatus is not in use. They therefore reduce the availability of the radiotherapy apparatus, for clinical use. Moreover, ceiling-mounted cameras tend to have a limited field of view, with components of the radiotherapy equipment and/or the patient him or herself often blocking their view of at least part of the patient support surface, in at least some of its possible positions/locations.

The present inventors have recognised that at least some of the above-mentioned deficiencies may be addressed by using sensors, or detectors, that are located below the level of a patient support surface, for example at or just above floor level. Typically, there will be very few (and sometimes no) components of radiotherapy equipment located between the floor and the patient support surface. Therefore floor-mounted (or low level) sensors tend to have an improved field of view, as compared to ceiling-mounted sensors. Moreover, the present inventors have recognised that certain sensor types may have particular associated benefits. For example, a system comprising appropriately-located optical or InfraRed (IR) markers and a corresponding optical or IR sensor may enable accurate and reliable position detection whilst being straight-forward and relatively inexpensive to implement, in practice.

Figure 3:
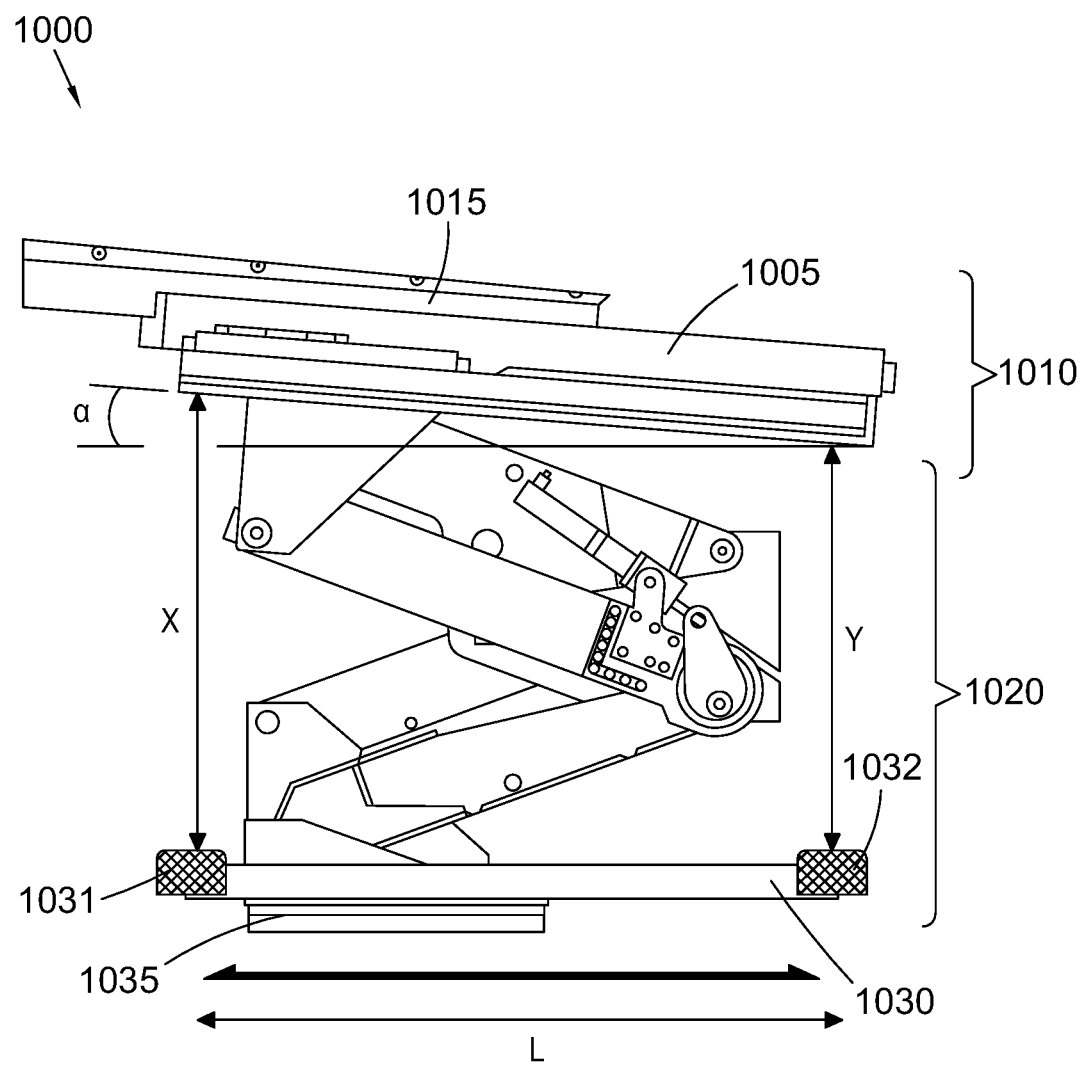
FIG. 3 shows an example of a patient positioning system.

FIG. 3 shows a patient positioning device 1000 that may be used to implement one or more of the improved methods described herein. The patient positioning device 1000 of FIG. 3 is shown by way of example only. Other arrangements are contemplated.

The patient positioning device 1000 may be comprised within a radiotherapy system that also includes radiotherapy treatment apparatus. The radiotherapy system may include components such as a gantry, as described above in relation to FIG. 1. The radiotherapy system may be located within a radiotherapy treatment room, which may also be referred to as a 'radiotherapy treatment environment'.

The patient positioning device 1000 comprises a patient support apparatus 1010 comprising a platform 1005 and a patient support surface 1015, wherein the platform 1005 is generally located below the patient support surface 1015. A patient may lie on the patient support surface 1015 when the patient positioning device 1000 is in use. As detailed further below, at least a portion of the patient support surface 1015 may be moveable with respect to at least a portion of the platform 1005, within the patient support apparatus 1010.

The patient positioning device 1000 further comprises a base 1030, which rests on or just above the floor. It also comprises a support structure 1020 to support the patient support apparatus 1010, above the base 1030.

Although not explicitly shown in FIG. 3, the device 1000 may comprise a rotation system that comprises one or more rotation mechanisms, which may take any appropriate form, for rotating the patient support surface 1015 about one or more of its axes. For example, the rotation system may be configured to tilt the patient support surface 1015, about a pitch axis. Alternatively or additionally, the rotation system may be configured to tilt the patient support surface 1015, about a roll axis and/or about a yaw axis. The rotation system may therefore be configured to cause and control rotation of the patient support apparatus by one or more of pitch, roll and yaw. The rotation system may be comprised of separate pitching, rolling and yaw mechanisms. Any suitable form(s) and operation(s) of the rotation mechanism(s) is/are contemplated. The patient support surface may be rotatable with its platform 1005, or independently of it.

The device 1000 further comprises a sensor arrangement. The sensor arrangement comprises a plurality of sensors, arranged below the patient support apparatus 1010. The sensor arrangement in FIG. 3 is provided on the base 1030, which itself is just above floor level The example shown in FIG. 3 comprises two sensors, but having just one sensor or having more than two sensors is contemplated and may be appropriate, at least in some embodiments. The plurality of sensors in FIG. 3 comprises at least a first sensor 1031 and a second sensor 1032. The first and second sensors 1031, 1032 are communicatively coupled to a processor (not shown). The sensors 1031, 1032 are arranged to send signals to the processor and, based at least in part on the received signals from the sensors 1031, 1032, the processor is configured to make determinations about the patient's position or location, as detailed further below.

Figure 6:
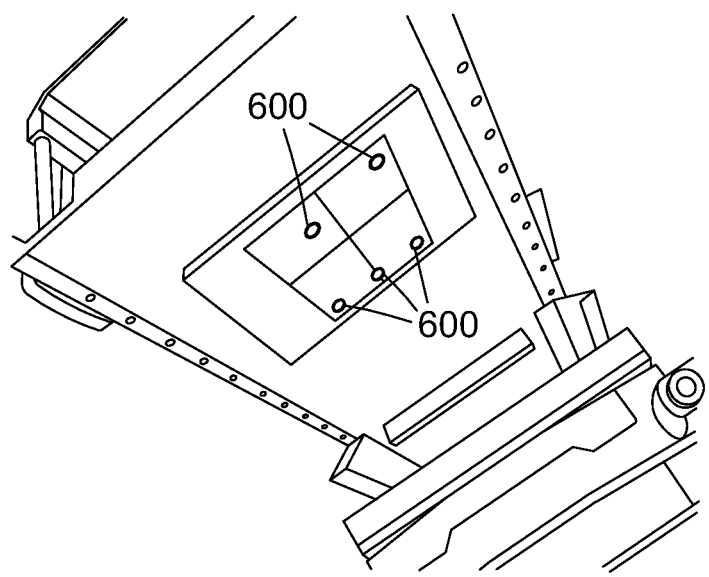
FIG. 6 shows a plurality of markers on an underside of a patient support surface.

Although not explicitly shown in FIG. 3, an underside of the patient support apparatus 1010 comprises a plurality of reference points or 'markers' that can be detected by at least one of the sensors 1031, 1032, as will be detailed further below. An example of an arrangement of such markers is shown in FIG. 6. The markers may be provided on an underside of the platform 1005 and/or on an underside of the patient support surface 1015. For example, they may be provided on a portion of the patient support surface 1015 that is moveable, for example slidably or rotatably moveable, relative to the platform 1005. This will be discussed in more detail, later in the present application.

Returning to the sensors 1031, 1032; in the example of FIG. 3, the first sensor 1031 is configured to provide signals indicative of a first distance, X, between a first region 1011 of the underside of the patient support apparatus 1010 and a first fixed location (of the first sensor 1031), underneath the patient support apparatus 1010. Similarly, the second sensor 1032 is configured to provide signals indicative of a second distance, Y, between a second region 1012 of the underside of the patient support apparatus 1010 and a second fixed location (of the second sensor 1032), underneath the patient support apparatus 1010. The first region 1011 and second region 1012 may correspond to first and second respective markers, on the underside of the patient support apparatus 1010. Distances X and Y may be described as being substantially 'vertical' distances, in the orientation of the device 1000 as shown in FIG. 3. It should be noted that an arrangement such as this, in which a first sensor 1031 senses one marker and a second sensor 1032 senses a second, different marker is just one possible example, and should not be regarded as limiting. As detailed further herebelow, one or more sensors in an arrangement, such as the sensors 1031, 1032 shown in FIG. 3, may in fact each be arranged to sense multiple markers on the underside of the patient support apparatus 1010.

Reference is made above to 'fixed locations' of the first 1031 and second 1032 sensors. In some arrangements, the locations of at least some of the sensors will be fixed (i.e. unchanging) within the radiotherapy treatment room. However, in some arrangements, the base 1030 of the patient positioning device 1000 may be configured to swivel or rotate, thereby rotating the entire patient positioning device 1000. An example of a rotator 1035, for rotating the patient positioning device 1000, can be seen below the base 1030 in FIG. 3. The rotator 1035 may comprise a turntable, which enables the entire table structure to be rotated about its 'yaw' axis, around the isocentre of the linac. In such an implementation, the term 'fixed location' or 'fixed position' of a sensor may mean fixed with respect to the base 1030, rather than fixed with respect to static features such as the floor or the walls of the treatment room. Other implementations are also contemplated, in which the locations of one or more sensors are not fixed per se but will be known, to the relevant processor, at the time or times at which they sense a marker or other reference point, on an underside of the patient support apparatus 1010. Therefore, rather than having 'fixed positions', the sensors may be regarded as having 'known positions'.

The sensors 1031, 1032 are configured to detect or sense the respective first and second markers (or first 1011 and second 1012 regions) on the underside of the patient support apparatus 1010, and to provide outputs from which the distances 'X' and 'Y' can be determined. Although in FIG. 3 it is indicated that the first sensor 1031 detects the first marker (in the first region 1011) and the second sensor 1032 detects the second marker (in the second region 1012), in some arrangements, at least one of the sensors may be configured to detect or sense a plurality of different markers. For example, a sensor may be provided that can detect the presence of any marker, at least within a predetermined distance from the sensor and/or at least within a predetermined area of the underside of the patient support apparatus 1010. For example, two or more different sensors may be arranged to detect or sense the same (i.e. an in-common) marker. For example, information regarding the position or location of the patient (and/or the patient support surface 1015) may be derivable from the relative positions (and/or from a difference in the relative positions) of a single marker, as sensed by two or more respectively different sensors. Moreover, having multiple sensors that can sense and provide feedback on the location of multiple markers, with some overlap therebetween, generally provides a level of redundancy that enables more precise determination of position and orientation.

The first and second known (or 'fixed') locations of the sensors may be located substantially at, within, or on, the base 1030 of the patient positioning device 1000. In FIG. 3, the sensors 1031, 1032 are positioned on the base 1030, such that distances and Y can be thought of as the distance between the regions 1011 and 1012, of the underside of the patient support apparatus 1010 and the base 1030, minus any systematic 'additional distance' introduced by the physical form of the sensors 1031, 1032, themselves, for example the height of the sensors 1031, 1032 above an upper surface of the base 1030. The physical form of the sensors 1031, 1032 in FIG. 3 is illustrative only. In practice, sensors may be used that are substantially flush with an upper surface of the base 1030—for example, they may be at least partially embedded in the base 1030—or that are relatively thin and do not extend significantly above the main upper surface of the base 1030. Arrangements are also contemplated in which the sensors are provided at floor level, for example embedded at least partially within the floor, or resting directly on the floor.

The sensors 1031, 1032 may be of any suitable type. For example, they may be optical sensors such as optical distance sensors. Such sensors are known to the skilled person and typically make use of pulsed light. In operation of an optical distance sensor; the strength (or intensity) of a returned signal from a target surface may be indicative of a distance between the sensor and the target surface. Alternatively, the time taken for a beam to be reflected from a target surface and return to the sensor may be used to determine the distance between the sensor and the target surface.

The distance values may be derivable by reference to calibration data, which may comprise a look-up table relating light signal intensity to distance values. The distance values may, alternatively or additionally, be derivable from one or more calculations carried out by a processor that receives signal information from the sensors.

In the example of FIG. 3, the first 1031 and second 1032 sensors comprise laser-based optical sensors. The sensors 1031, 1032 may be triangulation laser sensors. The sensors 1031, 1032 may be referred to as being 'laser metrology modules'. Laser metrology modules are known to be cost-effective, high performing and resistant to failure. They are therefore suitable for use in this context, as they should be reliable and should not require a back-up or redundancy provisions.

Examples of sensors suitable for implementing subject matter of the current application include the LAMM ('Laser Metrology Module') and the O-LAMM ('Orthogonal Laser Metrology Module') available from PLX Inc following acquisition of Reflex Imaging Ltd. While each LAMM scans along a single axis, the O-LAMM also scans along a second, orthogonal axis and enables full 3-dimensional, 6-degrees of freedom scanning capability. Such sensors are capable of providing distance measurements accurate to +/−0.1 mm at a sample rate of 500 Hz. In addition, the modularity and low cost of these sensors enable multiple of these sensors to be used in combination. These characteristics are suitable for putting the subject matter described in the current application into practice. These example devices are described merely to illustrate examples of available, suitable sensors. The subject matter of the current application can be carried out using any suitable sensors and is in no way limited to the example devices described above.

The value of distance 'X' can be derived from signals produced by the first sensor 1031 and the value of distance 'Y' can be derived from signals produced by the second sensor 1032, in this example. The markers or other reference points on the underside of the patient support apparatus 1010 represent the target surface(s) for the sensors 1031, 1032. The sensors 1032, 1032 may be (but do not necessarily need to be) used in conjunction with other appropriately placed optical devices such as (but not limited to) mirrors, light reflectors, and/or other targets.

As can be seen in FIG. 3, the sensors 1031,1032 are spaced from one another, along an axis that is substantially parallel to the 'major' axis (or 'roll' axis or 'length') of the patient support surface 1015 thereabove. The device 1000 is configured so that the distance between the two sensors 1031, 1032 is known, or can be measured or otherwise obtained, and may be fixed. As a result of the distance (i.e. the spatial separation) between the two sensors being known; the signals (or measurements) obtained by the two sensors 1031, 1032 can be used to obtain various data regarding the position or location of the patient support surface 1015, and thus regarding the position or location of at least part of the patient. As mentioned above and as will be detailed further below; this can be done before radiotherapy treatment begins and/or during radiotherapy treatment. The term 'during radiotherapy treatment', as used in this context, may be regarded as meaning 'whilst a radiotherapy treatment beam is being applied to a target area of a patient'. It may also or instead be regarded as meaning 'between the start and end of a session of radiotherapy treatment, but at a time at which a radiotherapy treatment beam is not actually being applied to a target area of a patient'. For example, it may refer to a pause or gap, between successive applications of a treatment beam, within a single radiotherapy session (or within a single radiotherapy appointment) for the patient.

The signals (or measurements) obtained by the two sensors 1031, 1032 can be used to determine position (or location) information that has arisen due to deliberate movement of one or more parts of the patient positioning device 1000, or to the deliberate movement or alteration of another aspect of a radiotherapy system, relative to the patient positioning device 1000. The term 'deliberate' in this context may be regarded as meaning movement implemented by one or more actuators, under control of a suitable processor for the radiotherapy system in which the patient positioning device is comprised. The signals can therefore be used to check that a particular movement or alteration has been implemented correctly. These determinations/checks can be based, for example, on trigonometric principles, with which the skilled reader will be familiar. For example, and as detailed further in co-pending GB patent application no. 2003561.4, in the name of Elekta Limited, the entirety of which is incorporated by reference, the signals from the sensors 1031, 1032 may be used by a processor to determine or measure a degree of tilt a, of the patient support apparatus 1010, relative to a substantially horizontal reference position. The degree of tilt a in this example is a measurement of the size, or extent, of a rotation of the patient support apparatus, about a 'pitch' axis 1110 (as shown in FIG. 2).

The processor, with which the sensors 1031, 1032 are communicatively coupled in this example, is configured to determine, based on signals from the sensors 1031, 1032, the degree of tilt (or 'pitch') of the patient support apparatus 1010. Assuming the top surfaces of both sensors 1031, 1032 are coplanar with one another, and if the sensors 1031, 1032 are separated from one another along the major axis of the base 1030 by a distance 'L', the degree of pitch, i.e. the pitch angle α, can be calculated using the following formula:

$$\alpha = \tan^{-1}\left(\frac{X-Y}{L}\right). \quad (1)$$

If the upper surfaces of the two sensors 1031, 1032 are not coplanar—i.e. if X≠Y when α=0, then the known height difference between the upper surfaces of the sensors can be incorporated into the calculation in order to calculate α. In practice, the processor may need to take other factors into account for the calculation, such as: the thickness of the patient support apparatus 1010 and/or of the patient support surface; whether and to what extent the patient support surface is extended away from the rest of patient support apparatus; any deviation of either marker away from being directly above its respective sensor, and so on. The particulars of the calculation may vary between respective radiotherapy systems and/or between different radiotherapy sessions and/or between different patients.

Figure 4:
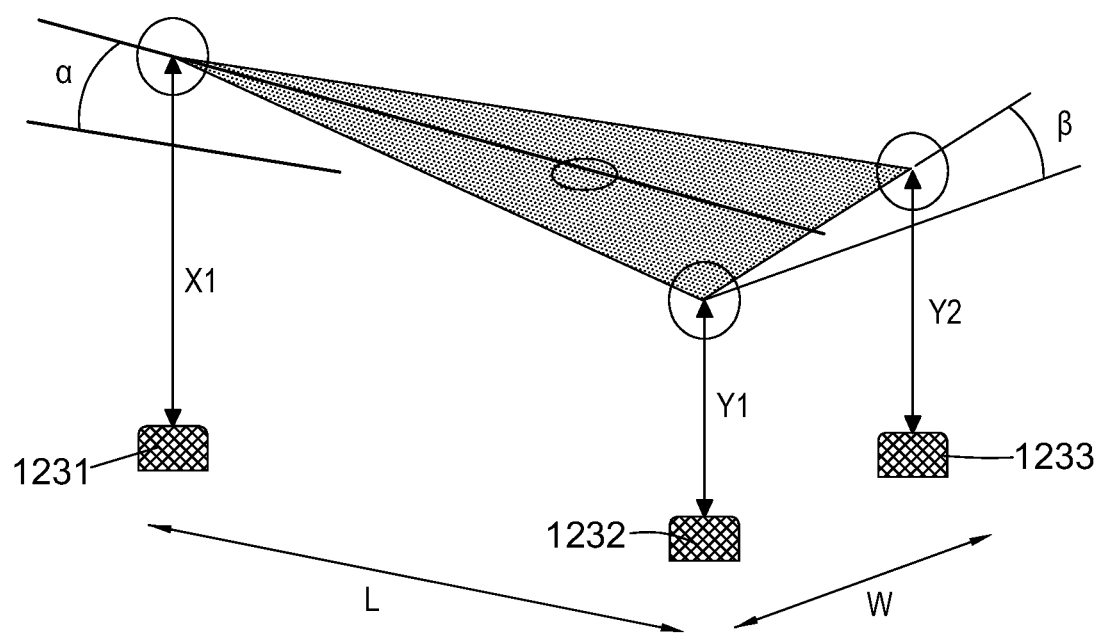
FIG. 4 shows three sensors for a patient positioning system.

As the skilled reader will appreciate, the number and locations of sensors that should be used for determining, measuring or checking the positions or locations of the patient support apparatus may depend on a number of factors. For example, the number and location of the sensors may depend on the number and type of degrees of freedom that the patient support apparatus 1010 has, for movement, and/or on the number and type of degrees of freedom that the patient support surface 1015 has to move, relative to the platform 1005 part of the patient support apparatus 1010. For example, FIG. 4 shows an arrangement of first 1231, second 1232 and third sensors 1233 that may be required for a patient positioning device (not itself shown), in which at least part of the patient support apparatus can be rotated about both its pitch axis and its roll axis. In FIG. 4, the degree of pitch, i.e. the pitch angle, is denoted by α. The degree of roll, i.e. the roll angle, is denoted by β. The three sensors 1231, 1232, 1233 are arranged to sense three respective substantially vertical distances, (X1, Y1, and Y2) each between itself and a corresponding marker or region thereabove.

A processor can be configured to determine, based on signals from the first 1231, second 1232, and third 1233 sensors, the degree of pitch and the degree of roll of the patient support apparatus 1010. Processing performed by the processor may make use of appropriate formulae, for example based on trigonometric principles. For example, α and β may be calculated as follows, wherein 'L' is the separation, along the pitch axis, of the first 1231 and second 1232 sensors, and 'W' is the separation, along the roll axis, of the second 1232 and third 1233 sensors:

$$\alpha = \tan^{-1}\left(\frac{X1 - \left(\frac{Y1+Y2}{2}\right)}{L}\right) \quad (2)$$

$$\beta = \tan^{-1}\left(\frac{Y2-Y1}{W}\right) \quad (3)$$

If the separations, L and W, between the two pairs of sensors (e.g. first to second and second to third) are known in a three sensor arrangement, and if each sensor is used to determine a height of a respective marker or region on the underside of the patient support apparatus; a co-ordinate in space can be defined for each of those three markers or regions of the underside of the patient support apparatus 1010. The three co-ordinates define a plane which may be used to describe a position in space of the patient support apparatus. Using simple geometry, the co-ordinates, and thus the height, of any point on the plane can be determined. Therefore, in this way, the position of a fourth region of the underside of the patient support surface can be determined based on the distances measured by the three sensors, even if there is no marker present in or on that fourth region.

In some arrangements, both pitch angle and roll angle could be determined by two sensors, if one of those two sensors sensed the locations of 2 markers, and the other sensed the location of a third marker. Or, indeed, a single sensor may in some cases be able to sense the location of 3 markers, to enable determination of both pitch and roll. In some arrangements, each of a plurality of sensors is configured to sense the location of the same 3 markers, in order to provide redundancy therebetween. Such an arrangement can enable a comparison to be made, of the sensed marker positions, and thus may provide higher confidence in the detected positions, and therefore of any detected rotations.

In some embodiments, the patient support apparatus may be configured to rotate about a yaw axis that extends into the plane of the diagram shown in FIG. 2. To measure a yaw angle, a sensor may be provided which is tilted, or else mounted horizontally, with respect to the patent support apparatus. This is in contrast with the sensors described above, which are substantially vertically mounted. If the yaw axis of rotation is fixed, one horizontally oriented sensor may be configured to determine the yaw rotation, using trigonometric principles similar to those described above. If the patient support surface is configured to provide a horizontal displacement of the apparatus and of the yaw axis, a second horizontally mounted sensor may be provided to distinguish between side-to-side movement and rotation. Such sensors may sit outside the patient positioning device, for example on a surface that is fixed within (or relative to) the radiotherapy treatment room.

In addition to measuring, determining or checking movements that have been made deliberately, the signals (or measurements) obtained by the two sensors 1031, 1032 can also be used to determine position (or location) information relating to non-deliberate movement of one or more parts of the patient positioning device 1000, or to the movement or alteration of another aspect of a radiotherapy system, relative to the patient positioning device 1000. The signals may also be used to determine any movements that may cause certain parts of a radiotherapy system to behave in non-ideal (or in mathematically irregular) ways. For example, the present inventors have recognised that real-world effects such as sag, flex, stress, strain and creep may be exhibited by parts of a radiotherapy system, in use, and may change the positions of aspects of the radiotherapy system, for example of the patient support surface. These real-world effects may be caused by physical forces such as gravity and friction, and/or by mechanical wear-and-tear or stress on the materials/structure of the components of the radiotherapy system. The present inventors have also recognised that anatomical changes in a patient, such as respiration and other involuntary processes, may also cause non-deliberate movement of a patient during radiotherapy treatment.

The changes caused by non-deliberate movement of a patient may be relatively small—in some cases, they may even be on a sub-millimetre scale. The present inventors have recognised that those changes may nonetheless have a material effect on the behaviour of a radiotherapy system and on the resulting accuracy of treatment, as well as on the calculations that should be performed for accurate delivery of radiotherapy treatment.

For example, the inventors have recognised that 'sag' (or deflection, or bending, or deformation) of a patient support surface can occur, due to a patient's weight, when the patient is mounted on the patient support surface 1015. This may be referred to as 'static' sag or static bending. Generally speaking; the extent of such static sag is dependent on the weight of a patient, with heavier patients causing greater static sag effects. Static sag, caused by a patient's weight, tends to take the form of substantially vertical dipping or sinking of some of the patient support surface.

The present inventors have also recognised that 'sag' (or deflection, or bending, or deformation) of a patient support surface can occur when some or all of the patient support surface is moved away from its support structure, and/or away from a substantially planar position. This may be referred to as 'dynamic' sag or dynamic bending, because it results from movement (or position change) and is generally dependent on the size and type of movement or change involved.

Figure 5:
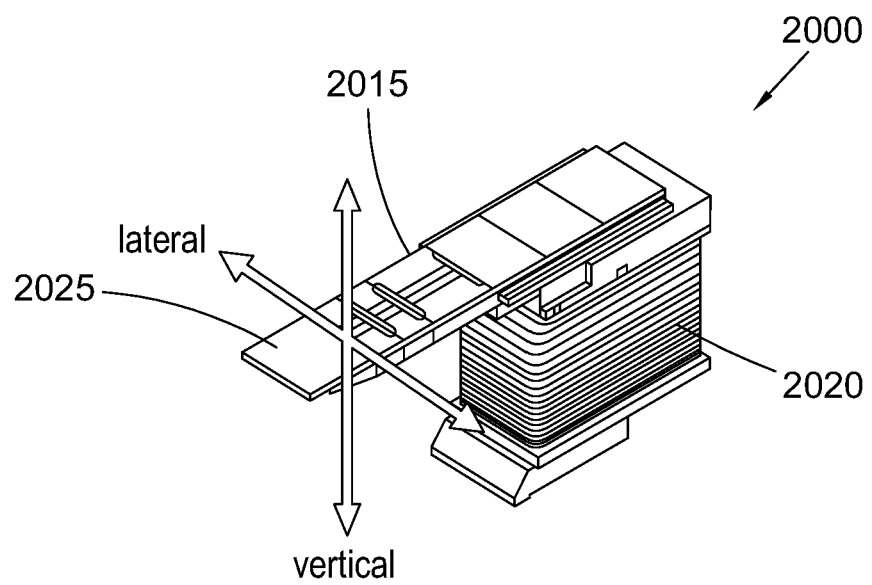
FIG. 5 shows non-linear bending of a patient support surface.

For example, FIG. 5 shows a patient positioning device 2000 in which a patient support surface 2015 is supported by a relatively large support structure 2020. The patient support surface 2015 is slideably moveable, relative to an upper surface of the support structure 2020, so that a distal end 2025 of the patient support surface 2015 can travel away from the support structure 2020. As the skilled reader will recognise; the further the distal end 2025 travels away from the support structure 2020, the more likely it is to sag. Moreover, if a section of the patient support surface 2015 is hingedly (or 'tiltably' or 'rotatably') moveable relative to the rest of the patient support surface 2015, so that the hinged section becomes located/positioned at a desired tilt angle, relative to the rest of the patient support surface 2015; at least part of that hinged section, distal to where it connects to the main body of the patient support surface 2015, is liable to sag. The sagging by the hinged section may be under its own weight, and/or under the weight of any part of the patient that rests thereon. Again, the extent of the sag may depend on the weight that the hinged section is supporting, and how large it is—i.e. how far away from the hinge a most distal end of the hinged section is located. Dynamic bending can take the form of vertical dipping or sinking of some of the patient support surface and may also comprise a rotational shift (i.e. a shift away from a substantially horizontal position for a 'flat' patient support surface or away from a desired tilt angle for a hinged section.)

As the skilled reader will recognise; for both dynamic and static bending, the nature of the patient support surface—including its size, shape, material, structure, manner of attachment to other components, and so on—can have an effect on exactly when and where it might sag, and by how much. This notwithstanding; the present inventors have recognised that sag of the patient support surface can, in general terms, cause the patient resting thereon to be positioned (or located) at a different point in space, as compared to the point in space that a processor might have calculated for it and/or intended it to occupy. Furthermore, sagging may cause the patient support surface 1015 to no longer behave as a planar object, but instead to be slightly bent (or 'dipped' or 'curved'). Again, the present inventors have recognised that such non-planar behaviour can have an effect on the calculations that it should perform, in relation to the patient support surface. For example, the trigonometric equations (1), (2), and (3) above are based on an inherent assumption that the patient support surface is planar. Although such trigonometric calculations may still be applicable and highly useful, the present inventors have recognised that some corrections or adjustments may have to be made, in relation to such calculations, to account for sag (and possibly to account for other real-world effects), at least in some situations. For example, if sagging is detected, a position that is detected by trigonometric calculations, and which assumes regular, planar movements of the patient support surface, may have to be regarded as being a small virtual sphere, rather than a point per se, in order to compensate for the deviation from 'ideal' planar (or regular) movement, that the sag is causing.

The present inventors have recognised that, in order to improve accuracy from a radiotherapy system, bearing in mind the extent of the movement capabilities within most such systems and the real-world effects that can cause additional movements, it is desirable to keep track of (i.e. to know) the actual position of a patient (and/or of a patient support surface or patient positioning surface) during radiotherapy treatment. This can be done on a continuous basis, and/or intermittently, and/or at or after a time or times at which specific events or actions occur. For example, a patient-specific treatment plan may require a patient to be moved one or more times, during a radiotherapy session. Such movement may be required in order to treat to or more different target regions or sub-regions, or to treat the same region or sub-region from different respective angles or using different respective beam types, or for reasons of patient comfort, and so on. A controller may control one or more actuators to implement this movement. The present inventors have recognised that it may be desirable to check actual patient position, after the actuators have moved the patient, to determine whether the patient actually is at the position or location that was desired by the controller, in accordance with the treatment plan.

The present inventors have further recognised that it can be desirable to implement additional patient (and/or patient support surface) movements, to account or compensate for any deviations that are detected, between a preferred (or intended) patient position at a given time, and an actual patient position at that time. For example, the controller for a radiotherapy system may be programmed to position the patient support surface at a defined position in space, however sag can cause a different position to be attained because of factors such as patient weight and distribution, extent of translational or rotational movements, and so on. The present inventors have recognised that performing actual position detection will enable an amount of sag to be determined and then corrected for, perhaps by adjusting the vertical axis for the radiotherapy system, to ensure the correct position in space for the patient support surface (and therefore of the patient anatomy) is achieved.

The present inventors have also recognised that, additionally, or alternatively, it can be desirable to make other changes, to account or compensate for any deviations that are detected, between a preferred (or intended) patient position at a given time, and an actual patient position at that time. For example, one or more changes may be made to calculations that a processor is arranged to make, based on signals received from one or more of the sensors in the patient positioning system/device. For example, changes may be made to the radiotherapy treatment apparatus, such as recalibrating or altering the steering properties one or more of its beams, to change the location of its beam isocentre. For example, a radiotherapy system may store any deviations between intended and actual position, in order to 'learn' from them, and thus to inform future calculations, and/or future movement instructions, in order to be more accurate for future operation.

Thus, an improved radiotherapy system and associated methods and apparatus are provided herein, which may comprise a feedback loop, for monitoring patient position before and during radiotherapy and for making determinations about whether any changes or adjustments should be made, to one or more spatial relationships between the patient and one or more aspects of the radiotherapy system, in order to achieve (or otherwise account for) a target position for the patient and/or the patient support surface.

At least in some arrangements, the improved radiotherapy system comprises one or more sensors that are located below a patient support surface, and which is/are arranged to sense or detect a location of a patient support surface, from underneath. The arrangement of the sensors may be similar to the arrangements of FIG. 3 or 4 herein, or may comprise any other suitable arrangement. The sensors may be optical sensors or cameras. The sensors may comprise laser metrology modules. As the skilled reader will know, laser metrology modules can be useful as they tend to be precise, robust, high performance and low cost.

The sensors are arranged to sense or detect the presence, and the location/position, of a plurality of markers, arranged on an underside of a patient positioning apparatus. For example, the markers may be arranged on an underside of the 'table' or 'couch' that forms the patient support surface and/or they may be arranged on an underside of a platform or support structure, with which the patient support surface attaches or from which it extends. The markers should be positioned, and arranged relative to one another, in a known manner. The radiotherapy system may be pre-programmed or calibrated with the positions of, and spatial relationships between, the markers, before a patient is supported on the patient support surface and thus before real-world effects such as sag, flex, stress, strain and so on are encountered. Alternatively or additionally, the radiotherapy system may be arranged to make an initial detection (or check) of the marker positions and their relative locations, before use of the system with a patient, in order to create and store reference locations of the markers.

FIG. 6 shows an example of a plurality of optical markers 600, arranged on the underside of a patient support surface. In this example, the markers comprises InfraRed (IR) markers 600. They may be passive IR markers or active IR markers. If they are active IR markers, they may be arranged to 'flash' or activate in a particular sequence or order, which would be recognisable to the corresponding sensors.

The sensors (not shown in FIG. 6) can be arranged to detect the position of the patient and/or of the patient support surface, based on the positions/locations of the markers 600, whilst the patient is mounted on the patient support surface. This can occur both before and during radiotherapy treatment. The sensors can be arranged to submit detection signals to a processor that is arranged to compare the detected marker positions (and thus the position of the patient and/or patient support surface) to a target position, as defined by a patient-specific radiotherapy treatment plan. Such a comparison can enable the processor to determine if any sag, flexes, stresses or strains of the patient support surface have occurred, for example due to the weight of the patient and/or due to a part of the patient support surface being insufficiently supported in a particular position. For example, sag, flexes, stresses or strains of the patient support surface may occur when a section of it is tilted upwards and/or when a distal end of the patient support surface has been extended relatively far from its support structure. For example, sag or flex of the support surface may be detected by a comparison of the positions, in space, of a plurality of markers. A sag may be indicated by one or more of those markers being situated vertically lower in space than expected, and/or vertically lower than some of its surrounding markers, on what would ideally be expected to be a substantially planar, surface. For example, if no pitch rotation had been prescribed for the patient support surface, the patient support surface would be expected to be substantially horizontally-oriented. Any sag may deflect at least some of the patient support surface away from being substantially horizontal.

The signals from the sensors can form part of a so-called 'feedback loop', to ensure that (or to at least check whether) the physical location of the patient (and/or the patient support surface) matches an intended (or 'target') position or location, in accordance with the patient's treatment plan, at a particular point in time or at (or before) a particular stage of the patient's radiotherapy treatment session. This may be referred to as checking if the patient's position or location matches his or her treatment 'prescription'.

The response to the sensor signals, within a feedback loop, may be to make adjustments to the patient's location, relative to the radiotherapy treatment apparatus, by moving the patient support surface and/or by moving another part of the radiotherapy system, in an attempt to better match the intended patient position or location. The required movements may be very small. This can be done by the controller sending appropriate instructions to one or more actuators, to move the patient.

The response to the sensor signals, within a feedback loop, may be to make other physical and/or computational adjustments, to the radiotherapy system, to ensure that the radiotherapy treatment beam is more accurately targeted at a target region or sub-region, based on the actual position of the patient at a particular time.

The signals from the sensors can be considered before and throughout a radiotherapy treatment session, to ensure ongoing accuracy of positioning (or at least accuracy of the knowledge of patient position). For example, the sensors can be used to check patient position relative to an image, such as a reference image on which a patient's treatment plan has been based. They may also be used to check current (or instantaneous) patient position against their position in a pre-treatment image, which was taken by imaging apparatus of a radiotherapy system before commencement of radiotherapy treatment.

The sensors may, as detailed hereabove, be positioned below a patient support surface in order to provide an improved field of view and to avoid unwanted detection of entities other than the patient support surface. The selection of the precise locations of the sensors for a particular radiotherapy set-up may depend on a number of factors including, but not limited to: the shape and size of the radiotherapy environment, the shape and size of the patient positioning apparatus including its support structure; the types and ranges of movement of the patient support surface; the shape, size and exact nature of the sensors themselves; and the number, location and arrangement of the markers that are to be detected. Consideration may also have to be given to the potential negative effects of radiation on the sensors. As the skilled reader will appreciate; such negative effects may be mitigated by suitable shielding and/or by locating the sensors relatively far from the source of the radiation—this fits in with locating the sensors below the patient support surface, for example on or close to the floor.

The sensors, and other parts of a radiotherapy system that comprises the sensors, may have to undergo calibration. This may happen, for example, daily, or before every new patient is treated, or according to another schedule. Such calibration may comprise, for example, calibrating the sensors to account for any systematic errors and/or to set to readings or measurements that correspond to a rest position—for example, corresponding to a zero tilt angle and/or to zero extension of the patient support surface, away from its support structure. Such calibration methods are known to the skilled person.

As described above, a patient positioning device, which includes a patient support surface and a support structure provided therebelow, may be rotatable. In some embodiments, at least one of the sensors is in a fixed location, within a radiotherapy treatment room (or radiotherapy environment'). This can be helpful for determining a position of the patient support surface when it has been rotated isocentrically, about its yaw axis, because the fixed sensor will not also rotate with the patient positioning device. Alternatively, or additionally, another device such as a standard potentiometer or encoder may be provided, to work in conjunction with one or more of the sensor(s), in order to measure this angle of rotation.

Figure 7:
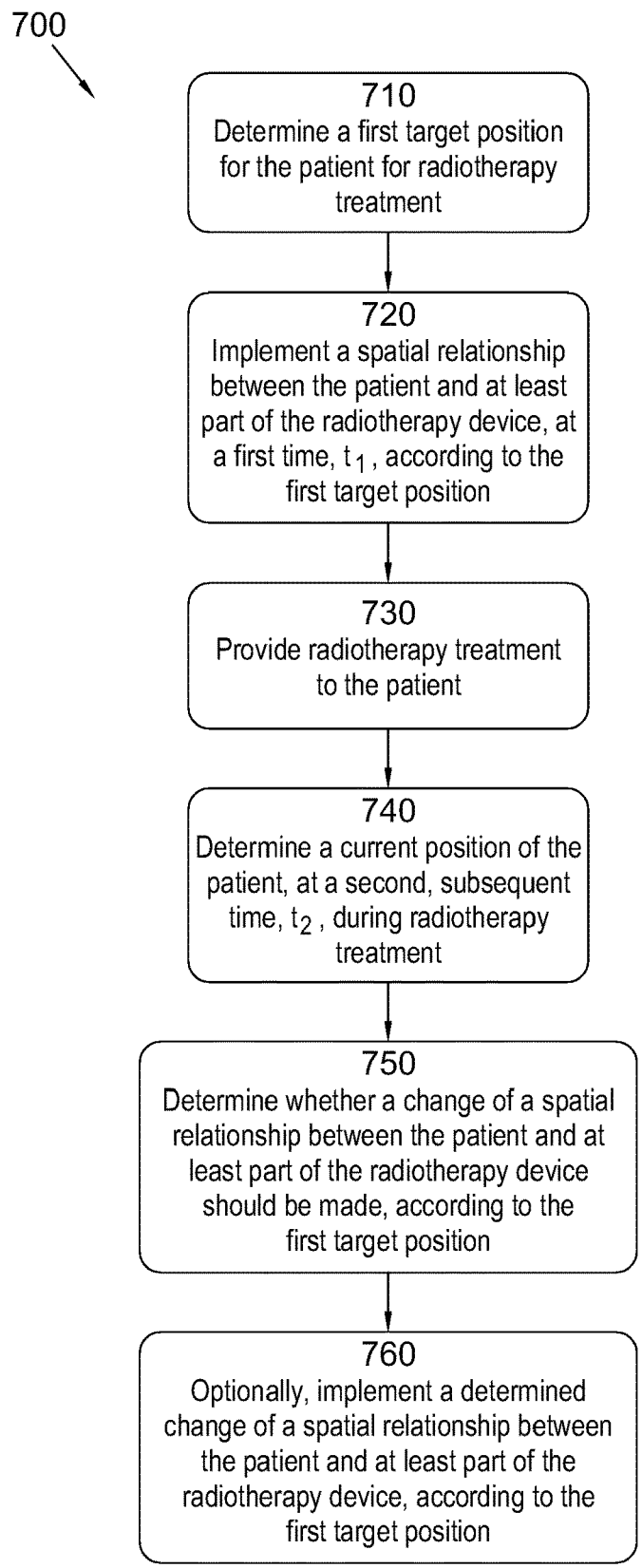
FIG. 7 shows an operational flow of a controller for a radiotherapy system.

FIG. 7 shows an example operational flow 700 of a feedback loop, which can be provided according to the improved system, methods and apparatus described hereabove. The feedback loop in this example is executed by a suitable controller that forms part of, or is communicatively coupled to, a radiotherapy system comprising: a radiotherapy device that includes radiotherapy treatment apparatus; a moveable patient support surface; one or more actuators for moving the moveable patient support surface, under control of the controller; a plurality of markers on an underside of the moveable patient support surface; and a plurality sensors below the underside of the moveable patient support surface, arranged to detect the plurality of markers.

At step 710, the controller determines a first target position for a patient for radiotherapy treatment. This may be determined by the patient's patient-specific radiotherapy treatment plan. The patient may already be mounted on the patient support surface, when this step is carried out. The first target position may be a target position for imaging the patient, for example for obtaining pre-treatment images before radiotherapy begins. The first target position may be a target position for radiotherapy treatment. Although referred to as a 'first' target position in FIG. 7, it is contemplated that the operational flow 700 could begin after a radiotherapy treatment session has already begun. Therefore the 'first' target position in step 710 may in fact comprise a 'next' or 'subsequent' position, to which the patient should be moved for radiotherapy treatment. The 'first' target position may, alternatively, simply comprise a target position for the patient, according to the treatment plan, at the current time, or at a specified future time.

At step 720, the controller issues an instruction to implement (i.e. to achieve) a spatial relationship between the patient and at least part of the radiotherapy device, at a first time $t_1$, according to the first target position. This step may inherently involve the controller determining or obtaining a current position of the patient (i.e. of the patient support surface), in order to determine whether a change should be made (and, if it is needed, what nature of change should be made) in order to position the patient at the first target position. The spatial relationship may be a spatial relationship (i.e. a relative position) between the patient's target area (i.e. a tumour or other region that is to be irradiated) and an isocentre of a treatment beam, produced by the radiotherapy treatment apparatus. The spatial relationship may be a spatial relationship (i.e. a relative position) between some or all of the patient support surface and a reference position or reference entity. Changing the spatial relationship may comprise controlling an actuator to move some or all of the patient support surface. Changing the spatial relationship may comprise moving something else, such as the treatment apparatus and/or a rotatable gantry on which the treatment apparatus may be located.

At step 730, radiotherapy treatment is provided to the patient. This may comprise commencement of radiotherapy treatment, for that session. This may comprise resumption of radiotherapy treatment, for that session. This may comprise continuation of radiotherapy treatment that was ongoing, during steps 710 and 720. Although not shown in FIG. 7, an optional step may be carried out before step 730, of checking that the patient is correctly located at the first target position, as a result of any change to a spatial relationship, which was made at step 720.

At step 740, which occurs during the radiotherapy treatment, the controller determines a current position of the patient, at a second time $t_2$ that is subsequent the above-mentioned first time $t_1$. The term 'during' radiotherapy treatment, as used in this context, should be regarded as meaning between the start and the end of a radiotherapy treatment session. The radiotherapy treatment beam may or may not actually be applied to the patient at the time at which step 740 is carried out. The step 740 of determining a current position of the patient may comprise obtaining a signal from one or more of the sensors regarding the position(s) of one or more of the markers, provided on an underside of the patient support surface. The step 740 may further comprises making one or more calculations, based on the received signals, or obtaining information from, for example, a look-up table, based on the received signals.

At step 750, it is determined whether a change of a spatial relationship between the patient and at least part of the radiotherapy device should be made, according to the first target position. This step is therefore a check as to whether the patient is (still) at the first target position, to which the controller issued instructions to move him or her. This step 750 may therefore comprise a comparison of the 'current' position, as obtained at the second time $t_2$, and the first target position. This step 750 may comprise both a check on whether any deliberate (usually relatively large-scale) movements were accurately executed by the actuator(s), for example to move the patient support surface to a target location, and a check on whether any non-deliberate (usually relatively small-scale) movements have occurred, for example due to sag, flex, stress, strain, creep and so on, of one or more parts of the radiotherapy system. Any change determined at step 750 may be in addition to a change that was previously made, at step 720.

It is possible that, at step 750, the controller will determine that the patient is located at the first target position, at least to within an acceptable margin of error or to at least an acceptable degree of certainty. If this is the case, the controller may choose not to make any changes to the radiotherapy system at that time. If, however, the controller determines a difference between the patient's current (at time $t_2$) position and the first target position, the controller can make decisions as to what should be done. Such a decision-making process may be entirely automated or semi-automated, for example based on a predetermined set of rules and/or restraints that the controller is programmed to follow. Alternatively, such a decision process may require some user-input, from the controller of the radiotherapy system. For example, the controller may be pre-programmed to operate autonomously until or unless certain thresholds are met or exceeded, at which point it may issue an alert to the user that input is required.

The controller may determine that a change in spatial relationship, between the patient and at least part of the radiotherapy device, should be made as a result of step 750. The controller may also determine the nature of that change. That is; the controller may determine what should be moved or changed, and by how much and in what direction, and so on.

At step 760, which is optional, the controller may implement a determined change of a spatial relationship between the patient and at least part of the radiotherapy device, according to the first target position. This may involve issuing instructions to move at least part of the patient support surface. This may involve issuing instructions to move or change another aspect of the radiotherapy system.

Alternatively or additionally, as a result of step 750, the controller may determine that one or more other changes should be made, to the radiotherapy system. Those changes may be physical and/or computational. For example, the controller may make an alteration to a calculation or to a formulae, which it employs with respect to its patient positioning apparatus. For example, it may account or compensate for a detected sag or flex of the patient support surface by changing a formula, and/or by amended an expected margin of error for a calculation. For example, the controller may change the routine or schedule for one or more of the sensors issuing signals to the controller, regarding the position(s) of one or more markers on the underside of the patient support surface. For example, it may prioritise the calculation of position based on certain signals, over respective others, in order to keep a closer eye on position changes to certain parts of the patient support surface and/or to ensure that certain positions are updated more frequently, in order to more accurately guide subsequent application of the radiotherapy treatment beam.

The flow (or method) of FIG. 7 may be repeated, during a radiotherapy treatment session. A continuous feedback loop may be implemented. Alternatively, the method 700 may be repeated at predetermined time intervals or at/after predetermined stages of the radiotherapy treatment session.

If the patient's treatment plan determines that he or she should be moved to a second, different, target position (or if any other circumstances arise that create a second, different target position for the patient), the steps of the method 700 may be repeated for that second, different target position. For example, if the controller detects sag or flex of the patient support surface, it may determine that the position or location to which the actuator should move the patient support surface should be altered, to account for that sag or flex and its impact on the actual location of a target region, within the patient. That altered or amended target position may be regarded as a 'second' (or, indeed, as a 'third' or any subsequent) target position, and the method 700 can be carried out for that altered or amended target position, accordingly.

Thus, an improved system, apparatus and methods are provided that enable enhanced monitoring of actual patient position before and during radiotherapy treatment, and which can enable alterations to be made in order to change, or compensate for or account for actual patient position, during radiotherapy treatment. Both large and small movements can be detected and taken into account. Moreover, both deliberate and non-deliberate movements can be detected and taken into account. The methods described herein can be applied both to static radiotherapy, for which a patient is still, when the treatment beam is applied, and for dynamic radiotherapy, for which the patient is continuously (or repeatedly) being moved, when the treatment beam is applied.

The improved system, apparatus and methods can enable a self-checking system to be provided, wherein a controller is responsible both for instructing one or more actuators to move a patient to a particular position or location, and also for checking that the patient is indeed at that position or location. The controller may also issue instructions for corrections to be made, if appropriate, based on any difference or discrepancy between a sensed actual patient position and a target patient position.

The improved system, apparatus and methods can be implemented on an existing radiotherapy system. That is; it is backwards compatible. It can be implemented for a wide range of different radiotherapy systems, both current and future.

The signals regarding patient position can be provided by sensors that are below an underside of a support surface or support apparatus, on which a patient is supported for radiotherapy. This enables the sensors to have a broad and largely uninterrupted field of view and to be able to detect a position of a patient support surface, regardless of how (and to where) it has been moved, within a radiotherapy environment. In addition, if the patient support surface were to vary in height, as a result of isocentric rotation, the operation of the sensors provided herein would be unaffected.

Because markers, such as optical markers, which the sensors are arranged to detect are provided underneath the patient support apparatus, there is no need to provide a frame or arch over the patient support surface, as has conventionally been required for known patient position sensing systems. This enables the radiotherapy system to be more streamlined overall. It can also enhance patient comfort, particularly for larger patients.

The sensors can provide signals indicative of a patient's (or at least of a marker's) real position, or location, in space. This can enable enhanced accuracy.

The sensors may comprises optical sensors, for example laser-based sensors. The sensors may be laser metrology modules. These are more reliable and provide more accurate position signals than other sensor types, such as electromechanical potentiometers and encoders, which are often found in know patient position sensing systems.

By using sensors configured to provide signals indicative of distances between regions of the underside of the patient support apparatus and known locations underneath the patient support apparatus, a direct measurement of the height, and thus position, of a patient support surface can be obtained. A relatively small number of sensors may be used, in order to accurately determine many facets of patient position, including height, side to side movement and any rotation or 'tilt'. Moreover, relatively small scale, usually non-deliberate (often unwanted) additional movements such as flex, sag, stress, strain and creep may also be detected by the same sensors as can detect the larger-scale movements that are caused deliberately by the actuator(s) within the radiotherapy system. The sensor arrangement thus provides a simple, cost effective, and accurate measurement arrangement.

In addition to the sensors described herein, other detectors devices may also be provided, to provide additional detection capabilities in relation to the position or location of a patient support surface, for radiotherapy treatment. For example, a sensor specifically arranged for sensing 'tilt' or 'incline' of a portion of the patient support surface may be provided. For example, it may comprise an electrolytic tilt sensors-based inclinometer and/or a gyroscope-based or magnetometer-based inclinometer. These will be familiar to the skilled reader.

Although the example arrangements shown and described herein comprise sensors provided on or close to the floor, below a patient support surface; other arrangements are also contemplated in which one or more sensors is provided above floor level, but still below an underside of the patient support apparatus. For example, a sensor may be provided on, within or close to a platform, such as the platform 1005 shown in FIG. 3 herein, which forms part of a patient support apparatus and relative to which at least part of a patient support surface thereabove can be tilted. Such a sensor may be used to measure a tilt angle of that part of the patient support surface, relative to the rest of it. A sensor may instead be provided on, close to or within a part of the support structure that extends substantially upwards from the base of a patient positioning device (and/or from the floor), and which supports a patient support surface thereabove.

Figure 8:
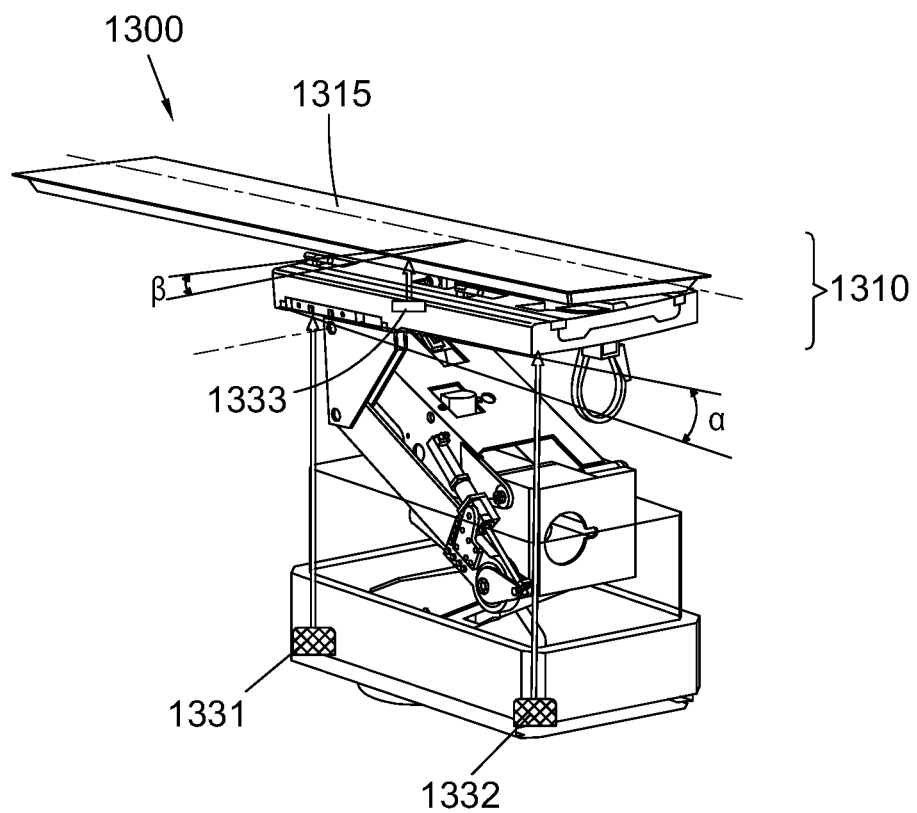
FIG. 8 shows an example of a patient positioning system with three position sensors.

FIG. 8 shows an example of one such arrangement, in which first 1331 and second 1332 sensors are provided on the base of a patient positioning device 1300, similarly to those described in relation to preceding figures. In addition, a patient support apparatus 1310, which is supported above the base and on which the patient is to be supported, comprises a third sensor 1333. The third sensor is positioned, in this example, between a base section of the patient support apparatus 1310 and the patient support surface 1315. The third sensor 1333 is similar in form and functionally to those described elsewhere herein, and is configured to measure a distance from a third fixed location to a region of an underside of the patient support surface 1315. Signals received from the sensor 1333 may be used to calculate the roll angle $\beta$. Accordingly, the third sensor 1333 may be referred to as a roll angle sensor or a roll rotation sensor. A single sensor in this layer may be used to determine the roll angle $\beta$ by virtue of a simple calibration process which creates a mapping between measured height values and tilt angles.

In some arrangements, it may be possible to provide sensors on an underside of a patient support apparatus and to provide corresponding markers, to be detected by those sensors, on the floor or on a base of a patient support device. The principles of position detection, monitoring and correction, as described in detail hereabove, could be applied to such an arrangement.

In some arrangements, one or more of the sensors may not be an optical sensor. For example, linear travel sensors, drawstring sensors, and/or draw wire sensors may be used. For example, a sensor for sensing isocentric (yaw axis) rotation may not be an optical sensor.

The improved methods described herein can be embodied on a computer-readable medium, which may be a non-transitory computer medium, which comprises computer executable instructions which, when performed by a processor, cause the processor to carry out the method.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

The above implementations have been described by way of example only, and the described implementations and arrangements are to be considered in all respects only as illustrative and not restrictive. It will be appreciated that the various aspects may be combined and used together, unless expressly described as being mutually exclusive. It will be appreciated that variations of the described implementations and arrangements may be made.

The invention claimed is:

1. A method of positioning a patient for radiotherapy treatment using a radiotherapy system, the method comprising:
   determining a first target position for the patient for radiotherapy treatment;
   implementing a spatial relationship between the patient and at least a part of a radiotherapy device, at a first time, according to the first target position;
   providing a radiotherapy treatment to the patient;
   determining a current position of the patient, at a second time, subsequent to the first time; and
   determining whether a change of the spatial relationship between the patient and at least a part of the radiotherapy device should be made, according to the first target position.

2. The method of claim 1, wherein determining a current position of the patient and determining whether a change of a spatial relationship between the patient and at least a part of the radiotherapy device should be made, according to the first target position, are repeated at a third time, subsequent the second time.

3. The method of claim 1, further comprising:
   implementing a change to the spatial relationship between the patient and at least a part of the radiotherapy device based on the determining of whether a change of the spatial relationship should be made.

4. The method of claim 1, further comprising:
comparing the current position of the patient, at the second time, and the first target position for the patient.

5. The method of claim 4, wherein the radiotherapy system comprises a controller, and the method further comprising:
determining whether a change should be made to at least one of a computation or a process that the controller is configured to carry out, based on the comparing of the current position of the patient, at the second time, and the first target position for the patient.

6. The method of claim 1, further comprising:
determining a second, different target position for the patient;
implementing a second spatial relationship between the patient and at least a part of the radiotherapy device for the second, different target position;
providing a second radiotherapy treatment to the patient at a third time;
determining a current position of the patient at a fourth time, subsequent to the third time; and
determining whether a second change of the second spatial relationship between the patient and at least a part of the radiotherapy device should be made, according to the second, different target position.

7. The method of claim 1, in which the first target position for the patient is comprised within a patient-specific treatment plan.

8. The method of claim 1, wherein the patient is supported by a patient support surface for radiotherapy treatment and wherein one or more sensors are provided, located below the patient support surface.

9. The method of claim 8, wherein determining a current position of the patient comprises receiving a signal from the one or more sensors located below the patient support surface and using the received signal to determine a position of at least part of the patient.

10. The method of claim 1, wherein determining a current position of the patient and determining whether a change of a spatial relationship between the patient and at least a part of the radiotherapy device should be made, according to a target position, are repeated multiple times, during radiotherapy treatment.

11. The method of claim 10, further comprising:
adjusting the target position, during radiotherapy treatment, and carrying out any subsequent determinations according to the adjusted target position.

12. The method of claim 1, wherein said method is a computer-implemented method.

13. A non-transitory computer-readable medium with instructions stored thereon which, when executed by a processor of a computing device, cause the processor to:
determine a first target position for a patient for radiotherapy treatment;
implement a spatial relationship between the patient and at least a part of a radiotherapy device at a first time, according to the first target position;
provide a radiotherapy treatment to the patient;
determine a current position of the patient at a second time subsequent to the first time; and
determine whether a change of the spatial relationship between the patient and at least part of the radiotherapy device should be made according to the first target position.

14. The non-transitory computer-readable medium of claim 13, wherein the instructions further cause the processor to:
implement a change to the spatial relationship between the patient and at least part of the radiotherapy device.

15. A radiotherapy system comprising:
a radiotherapy device; and
a controller;
wherein the radiotherapy device comprises:
a radiotherapy beam generation apparatus;
a moveable patient support surface;
an actuator for moving the moveable patient support surface; and
one or more sensors provided below an underneath surface of the moveable patient support surface;
wherein the controller is configured to: determine a first target position for the patient for radiotherapy treatment;
implement a spatial relationship between the patient and at least a part of the radiotherapy device, at a first time, according to the first target position;
provide radiotherapy treatment to the patient;
determine a current position of the patient, at a second time subsequent to the first time; and
determine whether a change of the spatial relationship between the patient and at least a part of the radiotherapy device should be made, according to the first target position.

16. The radiotherapy system of claim 15, wherein the controller is further configured to:
control actuation of the actuator in order to move the moveable patient support surface, according to the first target position for the patient for radiotherapy treatment.

17. The radiotherapy system of claim 15 wherein to determine current position of the patient and to determine whether a change of a spatial relationship between the patient and at least a part of the radiotherapy device should be made, according to the first target position, are repeated at a third time subsequent the second time.

18. The radiotherapy system of claim 15, wherein the controller is further configured to:
implement a change to the spatial relationship between the patient and at least a part of the radiotherapy device, wherein to implement a change to the spatial relationship includes to move the patient support surface, based on the spatial relationship, so as to move the patient relative to the radiotherapy beam generation apparatus within one or more degrees of freedom.

19. The radiotherapy system of claim 15, wherein the controller is further configured to:
compare the current position of the patient at the second time with the first target position.

20. The radiotherapy system of claim 15, wherein the controller is further configured to:
determine whether a change should be made to at least one of a computation or a process that the controller is configured to carry out, based on the comparison of the current position of the patient, at the second time and the first target position for the patient.

* * * * *